… …
7/15/86    XR    4,599,899

United States Patent [19]
Jero et al.

[11] Patent Number: 4,599,899

[45] Date of Patent: Jul. 15, 1986

[54] APPARATUS AND METHOD FOR CONTROLLING A SONIC DEVICE

[75] Inventors: John P. Jero, Washington; Michael A. Loda, Hanover Park; William L. Slusarek, Eureka, all of Ill.

[73] Assignee: Caterpillar Tractor Co., Peoria, Ill.

[21] Appl. No.: 701,836

[22] Filed: Feb. 14, 1985

[51] Int. Cl.$^4$ .................. G08B 21/00; G10K 11/00
[52] U.S. Cl. ........................... 73/584; 73/11; 228/103; 310/334; 340/657; 340/683
[58] Field of Search .............. 310/334; 73/11, 584; 340/654, 657, 683; 228/103

[56] References Cited

U.S. PATENT DOCUMENTS

| | | | |
|---|---|---|---|
| 3,489,241 | 1/1970 | Steinberg | 340/683 |
| 3,573,781 | 4/1971 | Shoh | 340/683 |
| 4,047,657 | 9/1977 | Mims | 228/103 |
| 4,472,970 | 9/1984 | Sundstrom | 73/584 |

Primary Examiner—Howard A. Birmiel
Attorney, Agent, or Firm—Stephen L. Noe

[57] ABSTRACT

An apparatus for controllably delivering power from a device to a workpiece is useful, for example, in performing qualitative material tests on various materials. In the instant apparatus, a sonic generator means controllably supplies sonic power to a workpiece, causing the surface of the workpiece to erode. A sensing means produces an actual power signal having a magnitude responsive to the power consumed by the sonic generator means. A settable means produces a desired power signal, and a control means compares the desired and actual power signals and supplies motor control signals in response to the respective magnitudes of the power signals and to a tracking time interval signal. In response to termination of the tracking time signal, the control means blocks the motor control signals. A motor means controllably moves the sonic generator means relative to the workpiece in response to receiving the motor control signals. Owing to the controllability of the apparatus, consistent, objective material test results are obtained from analysis of the power consumed by the sonic generator means with respect to time.

7 Claims, 6 Drawing Figures

APPARATUS AND METHOD FOR CONTROLLING A SONIC DEVICE

DESCRIPTION

1. Technical Field

This invention relates generally to an apparatus and method for controllably delivering power from a sonic device to a workpiece, and, more particularly, to an apparatus and method for performing qualitative tests on a workpiece by means of a sonic device.

2. Background Art

Sonic devices, used herein to include devices operating in the ultrasonic portion of the audio spectrum, are in common use in industry today. Such devices are often used in welding applications. For example, U.S. Pat. No. 3,573,781, issued Apr. 6, 1971 to Shoh, discloses an apparatus in which power is supplied to a sonic generator, converted into high frequency acoustical energy, and coupled to a workpiece being operated upon. The energy imparted to the workpiece, typically a thermoplastic material, causes localized heating of the workpiece and produces a weld.

A somewhat similar apparatus can be used for performing tests of material integrity and uniform material composition on various types of workpieces. For example, friction discs used in automotive clutch assemblies are frequently composed of sintered bronze. To obtain desired wear characteristics from the clutch discs, the bronze material must conform to predetermined specifications. In the past, it has been difficult to test such material characteristics in a reliable and consistent manner. It has been proposed that such material tests be performed by subjecting the workpiece to a source of sonic energy for a predetermined period of time. The absorbed energy causes a portion of the workpiece to be eroded, with the magnitude of erosion being related to physical characteristics of the workpiece. The eroded area or spot on the workpiece is subsequently evaluated by comparing it with known erosion patterns from both acceptable and unacceptable workpiece samples. A similar test procedure can be constructed for various other materials such as engine bearings.

Unfortunately, several problems or shortcomings are associated with the above-described procedure. The amount of sonic power delivered to the workpiece must be carefully controlled such that it remains constant from one test procedure to another. In both welding and material testing applications, the power is typically controlled by controlling the voltage supplied to the sonic generator while monitoring the amount of power consumed. However, a change in voltage causes a responsive change in the amplitude of the acoustical signal developed by the generator and a corresponding variation in the effect of the sonic power delivered to the workpiece. Therefore, the voltage supplied to the sonic generator should be maintained at a constant level.

Furthermore, the efficiency of the sonic generator varies in response to a number of factors. For example, mechanical connections within the sonic generator cause a certain amount of power to be dissipated internally rather than converted into acoustical energy. The amount of power so dissipated varies in relation to the particular generator being utilized, to the degree and frequency of maintenance the generator receives, to particular atmospheric conditions, and to various other factors. Any power so dissipated affects the validity of a material test or, alternatively, the quality of a weld. Therefore, such wasted or "null" power should be accounted for.

The aforementioned patent to Shoh recognizes, so far as welding applications are concerned, that delivery of less than a predetermined amount of acoustical energy to the workpiece being welded results in a defective weld. Shoh, therefore, measures the power consumed by the sonic generator, integrates the power measured during the welding process, and signals an alarm in the event that a predetermined minimum total amount of energy is not consumed over the total welding time. However, Shoh fails to exercise control over the process, or to address problems beyond the concern for the total power delivered in a welding application.

A further problem of particular concern in material testing applications is the subjective nature of the required analysis of the eroded area. Although the polar extremes of acceptable versus defective material may be readily apparent to one familiar with the testing process, the evaluation of materials between the extremes is quite difficult and unreliable. Therefore, an objective method of interpreting material test results is desired.

The present invention is directed to overcoming one or more of the problems as set forth above.

DISCLOSURE OF THE INVENTION

In one aspect of the present invention an apparatus for controllably delivering power from a device to a workpiece includes power supply means for supplying electric power to a sonic generator means. The sonic generator means controllably supplies sonic power to a workpiece in response to the power supply means. Means is provided for sensing the amount of power consumed by the sonic generator means and for producing an actual power signal having a magnitude responsive to the sensed power. Motor means controllably moves the sonic generator means relative to the workpiece in response to receiving motor control signals. Settable means is provided for producing a desired power level signal having a controlled magnitude, and control means is provided for comparing the magnitudes of the desired and actual power signals, delivering motor control signals to the motor means in response to the magnitudes of the compared power signals during a predetermined tracking time period, and blocking the delivery of the motor control signals to the motor means in response to termination of the tracking time period.

In a second aspect of the present invention, a method for testing a workpiece includes delivering an electric current at a substantially fixed voltage from a power supply to a sonic generator means. A sonic vibration is produced at a predetermined frequency and amplitude in response to receiving the electric current. The amount of power consumed by the sonic generator means is sensed, and the sonic generator means is moved relative to the workpiece in response to the sensed power failing to substantially equal a predetermined desired power level, and to a predetermined period of time. Movement of the sonic generator means relative to the workpiece is blocked in response to termination of the predetermined period of time, and the amount of power consumed by the sonic generator means is substantially continuously displayed.

The present invention provides accurate control of the amount of sonic power delivered to a workpiece, and offers reliable and repeatable material quality test results without variation caused by fluctuating power supply voltage. The power delivered to the workpiece is independent of any null power consumed by the sonic generator means. In addition, subjective analysis of the test results is eliminated and replaced by objective criteria.

BRIEF DESCRIPTION OF THE DRAWINGS

For a better understanding of the present invention, reference may be made to the accompanying drawings, in which.

BEST MODE FOR CARRYING OUT THE INVENTION

Figure 1:
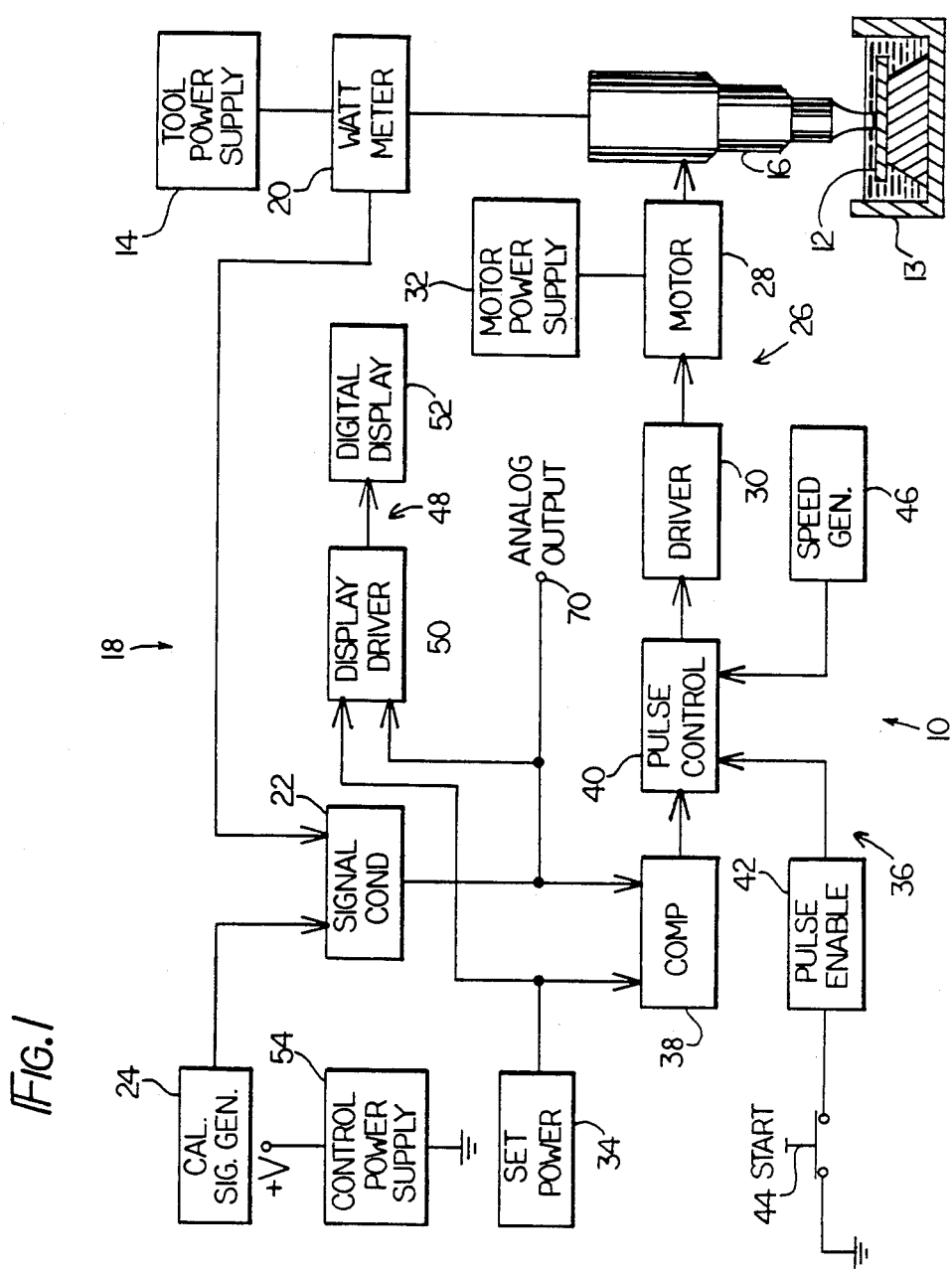
FIG. 1 is a block diagram of one embodiment of the present invention.

Referring first to FIG. 1, an apparatus embodying certain of the principles of the present invention is generally indicated by the reference numeral 10. It should be understood that the following detailed description relates to the best presently known embodiment of the apparatus 10. However, the apparatus 10 can assume numerous other embodiments, as will become apparent to those skilled in the art, without departing from the appended claims.

The apparatus 10 is shown in conjunction with a workpiece 12, for example, a bronze friction disc or other material to be tested. The workpiece 12 is preferably supported in an oil filled tank 13, with the workpiece 12 being completely submerged in the oil.

A sonic power supply means 14 delivers electric power to a sonic generator means 16. The sonic generator means 16 is, for example, a commercially available unit of the type produced by the Branson Sonic Power Company, Miry Brook Road, Danbury, Conn., as Model No. 184 V. Such sonic devices typically utilize piezoelectric members to convert power from an electric power supply into sonic energy or vibrations. The lower end portion of the sonic generator means 16 is positioned with respect to the workpiece 12 such that the oil in the tank 13 acoustically couples the sonic energy produced by the sonic generator means 16 to the workpiece 12.

Means 18 senses the amount of power consumed by the sonic generator means 16 and produces an actual power signal having a magnitude responsive to the sensed power. Means 18 includes a watt meter 20 interposed between the sonic power supply means 14 and the sonic generator means 16. The watt meter 20 is connected to a signal conditioner 22. A calibration signal generator 24 is also connected to the signal conditioner 22.

Motor means 26 is provided for controllably moving the sonic generator means 16 relative to the workpiece 12 in response to receiving motor control signals. The motor means 26 includes a motor 28 operatively connected to the sonic generator means 16. The motor 28 has associated with it a driver 30 and a motor power supply 32. In the preferred embodiment, the motor 28 is a stepping motor and the associated driver 30 is a translator circuit for the stepping motor. The stepping motor and translator circuit are, for example, of the type produced by The Superior Electric Company of Bristol, Conn. as Model Nos. M061-FD-6002 and STM101, respectively.

Settable means 34 for producing a desired power signal having a controlled magnitude is connected to the control means 36. The control means 36 compares the magnitudes of the desired power and actual power signals, delivers motor control signals to the motor means 26 in response to the magnitudes of the compared power signals during a predetermined tracking time period, and blocks delivery of the motor control signals to the motor means 26 in response to termination of the tracking time period. The control means 36 includes a comparator 38 connected to both the signal conditioner 22 and the settable means 34. The comparator 38 is also connected to a pulse control circuit 40 and to a pulse enable circuit 42. A start switch 44 is connected to the pulse enable circuit 42 which, in turn, is connected to the pulse control circuit 40. A speed generator circuit 46 is also connected to the pulse control 40. An output terminal of the pulse control circuit 40 is connected to the stepping motor driver 30.

A display means 48 includes a display driver 50 and a digital display 52. The display driver 50 is connected to the signal conditioner 22 and to the settable means 34. A control power supply 54 is included to provide general circuit power for the various elements discussed above. The control power supply 54 includes a positive or +V terminal and a negative or ground terminal.

Figure 2:
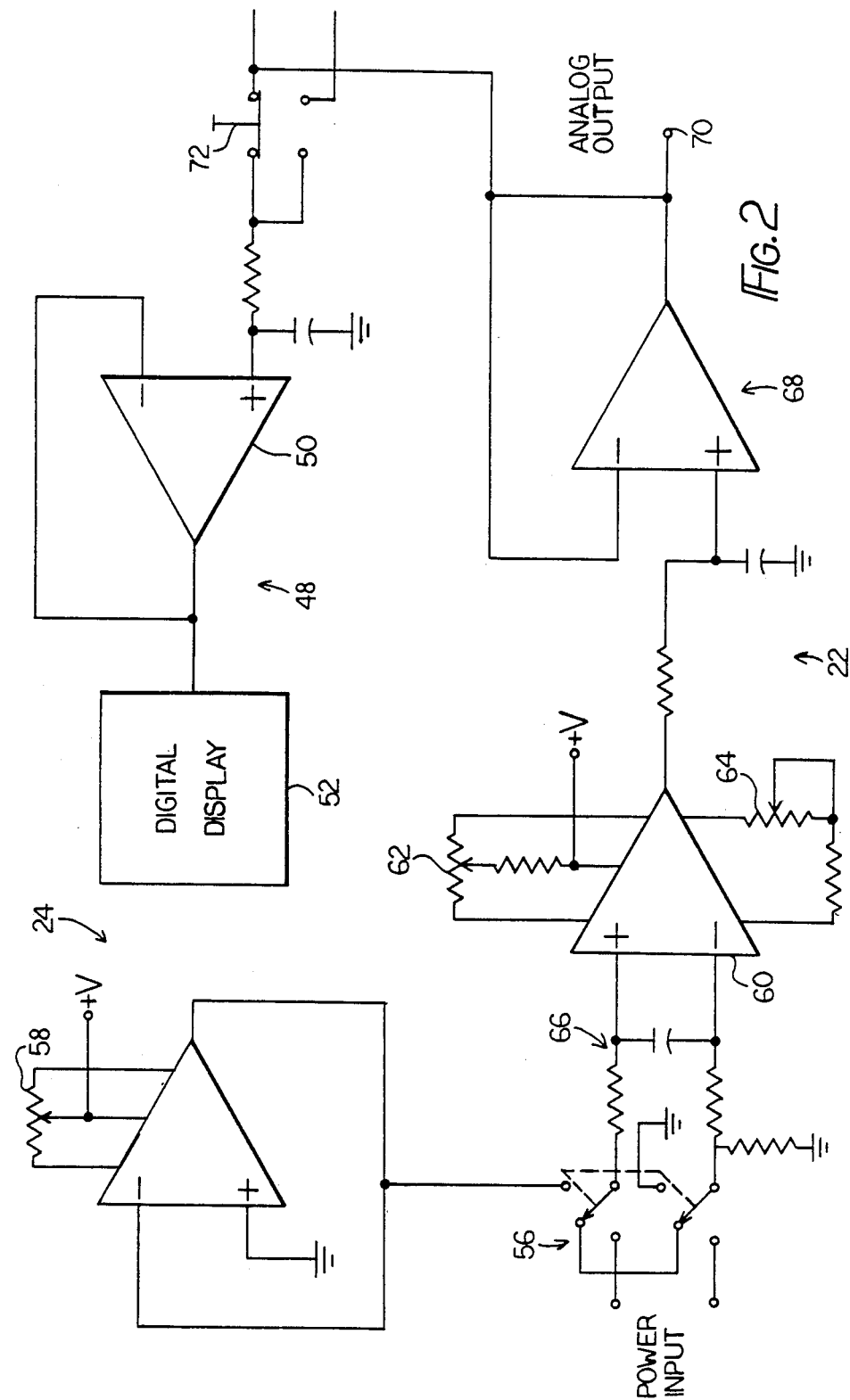
FIGS. 2, 3, and 4 collectively comprise a schematic diagram of the embodiment of the invention shown in FIG. 1.
Figure 3:
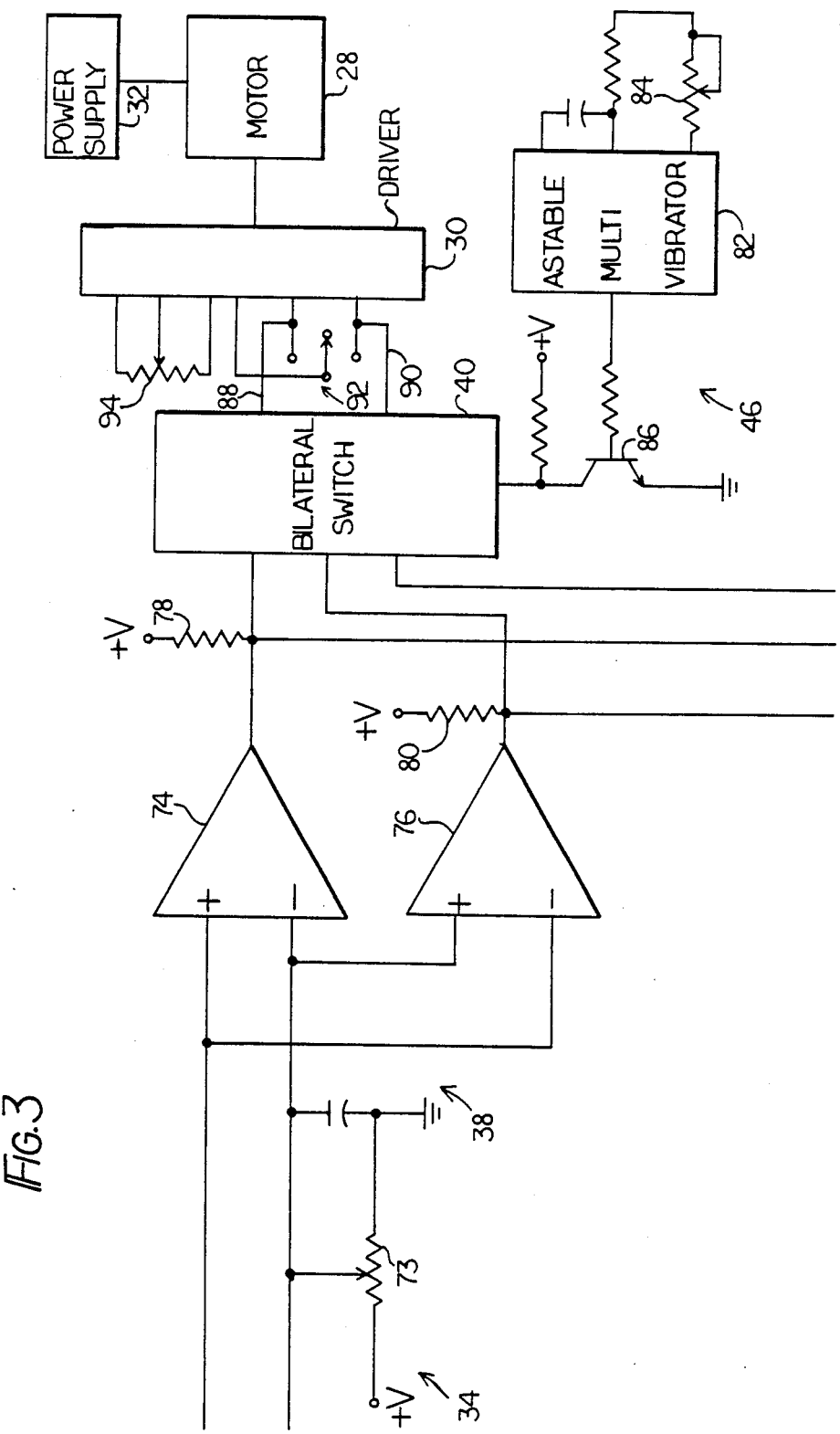
Figure 4:
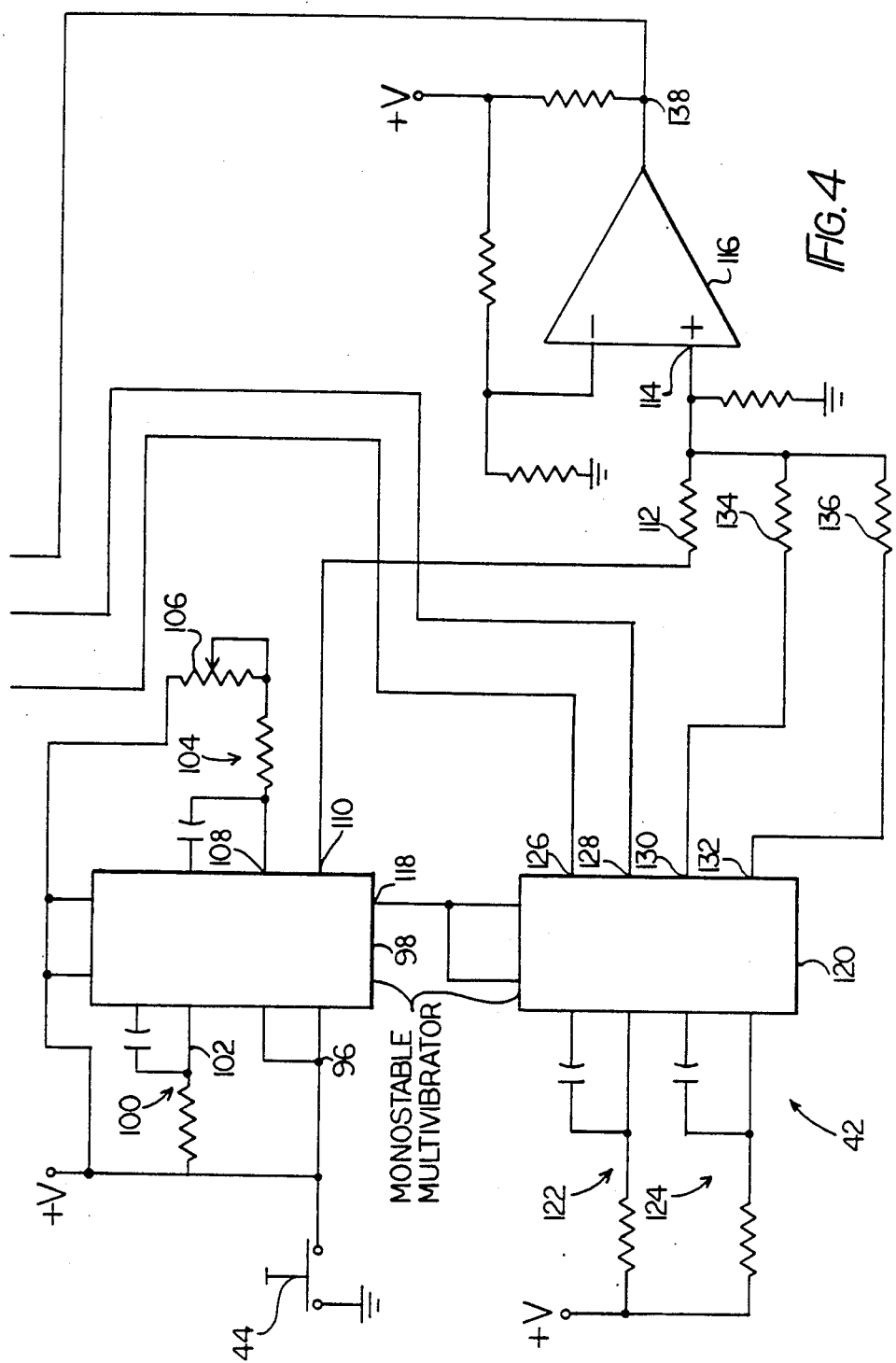

Reference is now made to FIGS. 2, 3, and 4, in which a schematic representation of the elements shown in block form in FIG. 1 is provided. Beginning with FIG. 2, a power signal from the watt meter 20 is delivered to a set of "power input" terminals of a selector switch 56. Owing to the fact that the watt meter 20 is connected intermediate to the sonic power supply 14 and the sonic generator means 16 (as shown in FIG. 1), the power signal delivered to the switch 56 is representative of the total power consumed by the sonic generator means 16. The power signal delivered to the power input terminals varies, for example, from 0 to 10 millivolts in response to power consumption by the sonic generator means 16 of 0 to 1,000 watts.

A second set of terminals of the selector switch 56 is connected to the calibration signal generator 24 and to ground. The calibration signal generator 24 is preferably a constant voltage source of conventional design, and delivers a signal to the selector switch 56 having a stable predetermined magnitude responsive to the adjustment of a calibration potentiometer 58. The output voltage supplied by the calibration signal generator is, for example, fixed at 2.5 millivolts.

The wiper associated with each pole of the selector switch 56 is connected to a respective input terminal of a first operational or differential amplifier 60. A zero adjust potentiometer 62 and span adjust potentiometer 64 are each connected to the first operational amplifier 60. A capacitor/resistor network 66 connected to the input terminals of the first operational amplifier 60 provides a passive low pass filter through which the signal delivered from the selector switch 56 passes. The output signal delivered from the first operational amplifier 60 passes through a buffer amplifier 68 connected as a voltage follower, the output of which is connected to an analog output terminal 70. Therefore, the signal selected by the selector switch 56 is conditioned by the first operational amplifier 60 and associated circuitry, and is delivered as an actual power signal to the analog output terminal 70. The first operational amplifier 60, buffer amplifier 68, and associated components are included in the signal conditioner 22.

The analog output terminal 70 is also connected through a calibration switch 72 to the display driver 50 of the display means 48. The display driver 50 includes an operational amplifier connected as a voltage follower, the output of which is connected to the digital display 52. The digital display 52 is, for example, a conventional three digit, seven segment LED display voltmeter module.

Referring next to FIG. 3, the analog output terminal 70 is connected to complementary input terminals of the comparator 38. The comparator 38 preferably includes second and third operational amplifiers 74,76. An alternate input terminal of each of the second and third operational amplifiers 74,76 is connected to a power select potentiometer 73. The power select potentiometer 73 is part of the settable means 34, and supplies a desired power signal having a controlled magnitude to the comparator 38. The desired power signal is also delivered to the calibration switch 72.

The output terminals of the second and third operational amplifiers 74,76 are preferably of the open collector type, and are connected, in conjunction with pull up resistors 78,80, to the pulse control circuit 40. The pulse control circuit 40 is, for example, a quad bilateral switch having an industry type number 4066.

The speed generator 46 is also connected to the pulse control circuit 40. The speed generator 46 preferably includes an astable multivibrator 82, for example, an industry standard type 4047. The output signal produced by the astable multivibrator 82 is a square wave signal having a frequency determined by the adjustment of a speed potentiometer 84, connected to the multivibrator 82. The square wave signal is coupled through a driver transistor 86 to the pulse control circuit 40.

Output terminals 88,90 of the pulse control circuit 40 are connected to respective input terminals of the motor driver 30, and to respective terminals of a motor direction switch 92. A manual motor speed adjustment potentiometer 94 is also connected to the motor driver 30. The motor driver 30 is connected to the stepping motor 28, as is the motor power supply 32.

Referring next to FIG. 4, the pulse enable circuit 42 is described. The start switch 44 is connected to a first input terminal 96 of a first monostable multivibrator 98, for example, an industry standard type 4047. A first R/C time delay circuit 100 is connected to a second input terminal 102 of the first monostable multivibrator 98. The first R/C time delay circuit 100 has, for example, a time constant of 10 seconds. A second R/C time delay circuit 104 includes a tracking time potentiometer 106, and is connected to a third input terminal 108 of the first monostable multivibrator 98. A first output terminal 110 of the first monostable multivibrator 98 is connected through a resistor 112 to a first input terminal 114 of a fourth operational amplifier 116.

A second output terminal 118 of the first monostable multivibrator 98 is connected to a second monostable multivibrator 120. The second monostable multivibrator 120 is similar to and of the same type as the first monostable multivibrator 98. The input terminals of the second monostable multivibrator 120 are connected to +V through respective third and fourth R/C time delay circuits 122,124. Each of the third and fourth time delay circuits 122,124 have time constants of, for example, 10 seconds. Third and fourth input terminals 126,128 of the second monostable multivibrator 120 are connected to respective ones of the second and third operational amplifiers 74,76, shown in FIG. 3.

First and second output terminals 130,132 of the second monostable multivibrator 120 are connected through respective resistors 134,136 to the input terminal 114 of the fourth operational amplifier 116. A gate output terminal 138 of the fourth operational amplifier 116 is connected to the pulse control circuit 40, also shown in FIG. 3.

Power supply connections, decoupling capacitors, unused or static terminal connections, and other components and connections commonly associated with industry standard components of the type herein described, are omitted from the drawings for purposes of clarity. It will be appreciated by those skilled in the art that information relating to such components and connections is well-known and readily available in texts and manufacturer's data sheets relating to the instant components. It will likewise be appreciated that the ratings, values, and manufacturers shown for various electrical elements discussed above are for exemplary purposes only. Alterations of the circuit and embodiment discussed, and the use of electrical elements of different constructions or ratings will be readily apparent to those skilled in the art. Such alterations or substitutions can be implemented without departing from the appended claims.

Industrial Applicability

Operation of the apparatus 10 is described with reference to the use of the apparatus 10 for controllably operating a device to test a workpiece, for example, a bronze friction disc. The friction disc or workpiece 12 is placed in an oil filled tank 13 and suspended in such a manner that the surface of the workpiece 12 is covered by a predetermined depth of oil. The sonic generator means 16 is raised away from the workpiece 12 and out of contact with the oil in the tank 13, by means of the motor direction switch 92. The speed at which the motor direction switch 92 operates the motor 28 is determined by the adjustment of the manual motor speed adjustment potentiometer 94, in cooperation with the motor driver 30.

A display device, preferably a chart recorder, is connected to the analog output terminal 70. Power is applied to the apparatus 10 from the control power supply 54, and the sonic generator means 16 is automatically driven away from the workpiece 12 for a period of 10 seconds, at a speed controlled by the speed generator 46, indicating that the apparatus 10 is operational and providing a visual indication of the adjustment of the speed potentiometer 84. The manner in which this occurs automatically is discussed below.

The selector switch 56 is placed in the "zero" position and the zero adjust potentiometer 62 is adjusted to provide a zero reading on the digital display 52. The chart recorder zero adjustment is also made at this time. The selector switch 56 is next placed in the "calibrate" position, which supplies the 2.5 millivolt signal from the calibration signal generator 24 to the input of the signal conditioner 22. The 2.5 millivolt signal is amplified by the signal conditioner 22 and displayed on the digital display 52. The span adjust potentiometer 64 is adjusted to produce a reading on the digital display 52 of "250", corresponding to a power level of 250 watts. In like manner, the chart recorder is adjusted to an appropriate scale reading. The apparatus 10 is thus calibrated such that a 1 millivolt signal delivered to the signal conditioner 22 produces an output signal at the analog output terminal 70 corresponding to 100 watts of power.

With the sonic generator means 16 positioned away from the workpiece 12 or in "free air", the selector switch 56 is set in the "run" position and the sonic power supply 14 is energized. Ideally, the sonic generator means 16 consumes no power at this time, owing to the fact that it is not acoustically coupled to the workpiece 12. However, power losses caused by the construction and maintenance of the sonic generator means 16, as well as other factors, cause some power to be consumed. This power, referred to herein as "null" power, is sensed by the watt meter 20 and delivered to the signal conditioner 22. The magnitude of the null power consumed by the sonic generator means 16 is responsively displayed on the digital display 52.

After noting the magnitude of null power displayed, the calibrate switch 72 is depressed, connecting the settable means 34 to the display means 48. Responsively, the magnitude of the desired power signal selected by the power select potentiometer 73 is displayed on the digital display 52. Assuming, for exemplary purposes, that it is desired to operate the material test utilizing an actual power of 250 watts, the power select potentiometer 73 is adjusted to display an indication of 250 watts plus the previously-noted null power value. For example, assuming a null power value of 50 watts, the power select potentiometer 73 is adjusted until a desired power signal having an equivalent magnitude of 300 watts is displayed.

The sonic power supply 14 is next deenergized, the calibrate switch 72 is released, and the sonic generator means 16 is manually positioned in close proximity to the workpiece 12, for example, approximately 1 millimeter from the surface of the workpiece 12. The sonic power supply 14 is again energized and the start switch 44 is depressed. Alternatively, a remote start switch having contacts in parallel with those of the start switch 44 can be utilized.

Figure 5:
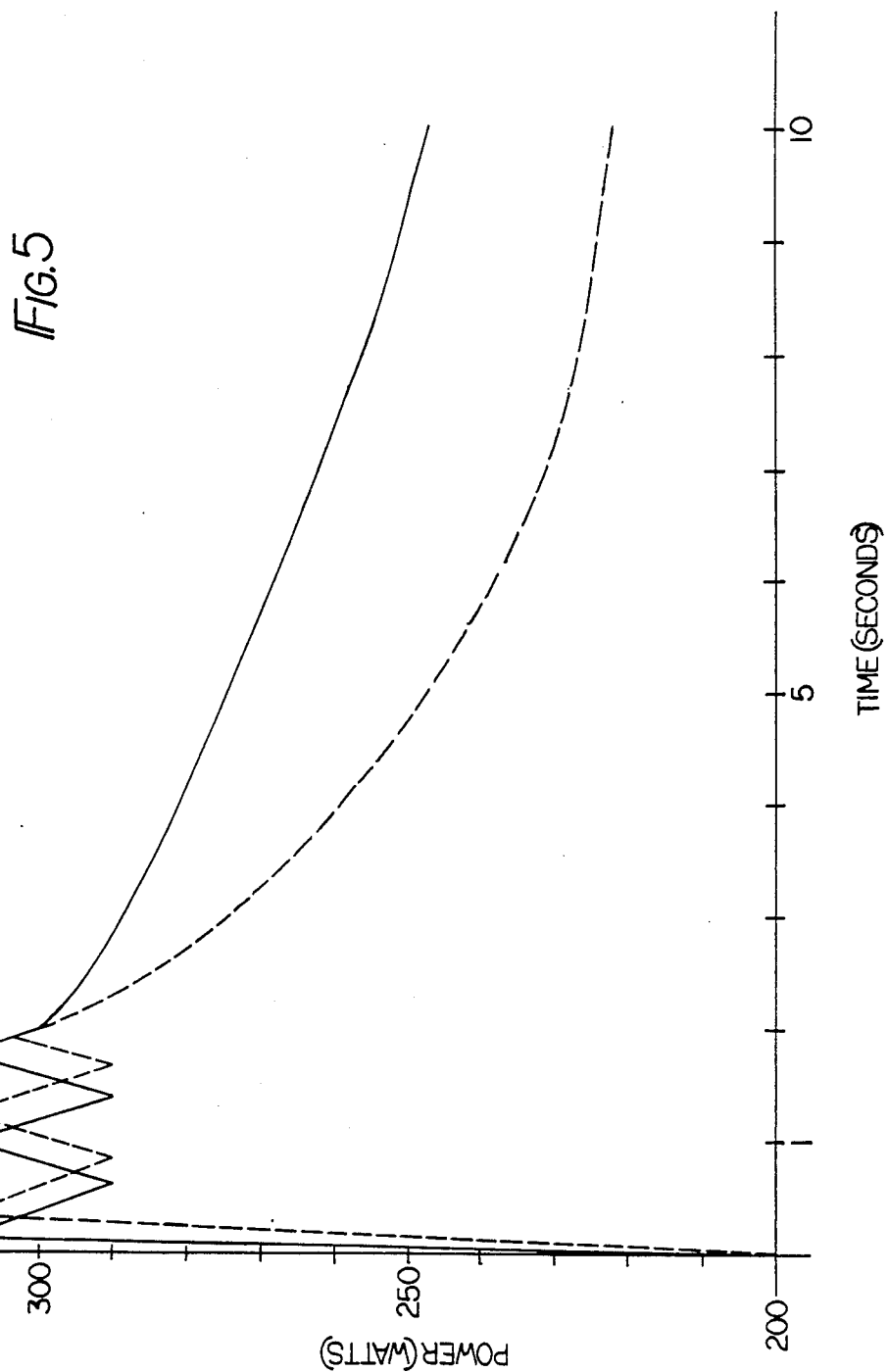
FIG. 5 is a graphic representation of data produced by the embodiment shown in FIG. 1; and, FIG. 6 is a signal timing diagram used to explain the schematic diagram shown in FIGS. 2, 3, and 4.
Figure 6:
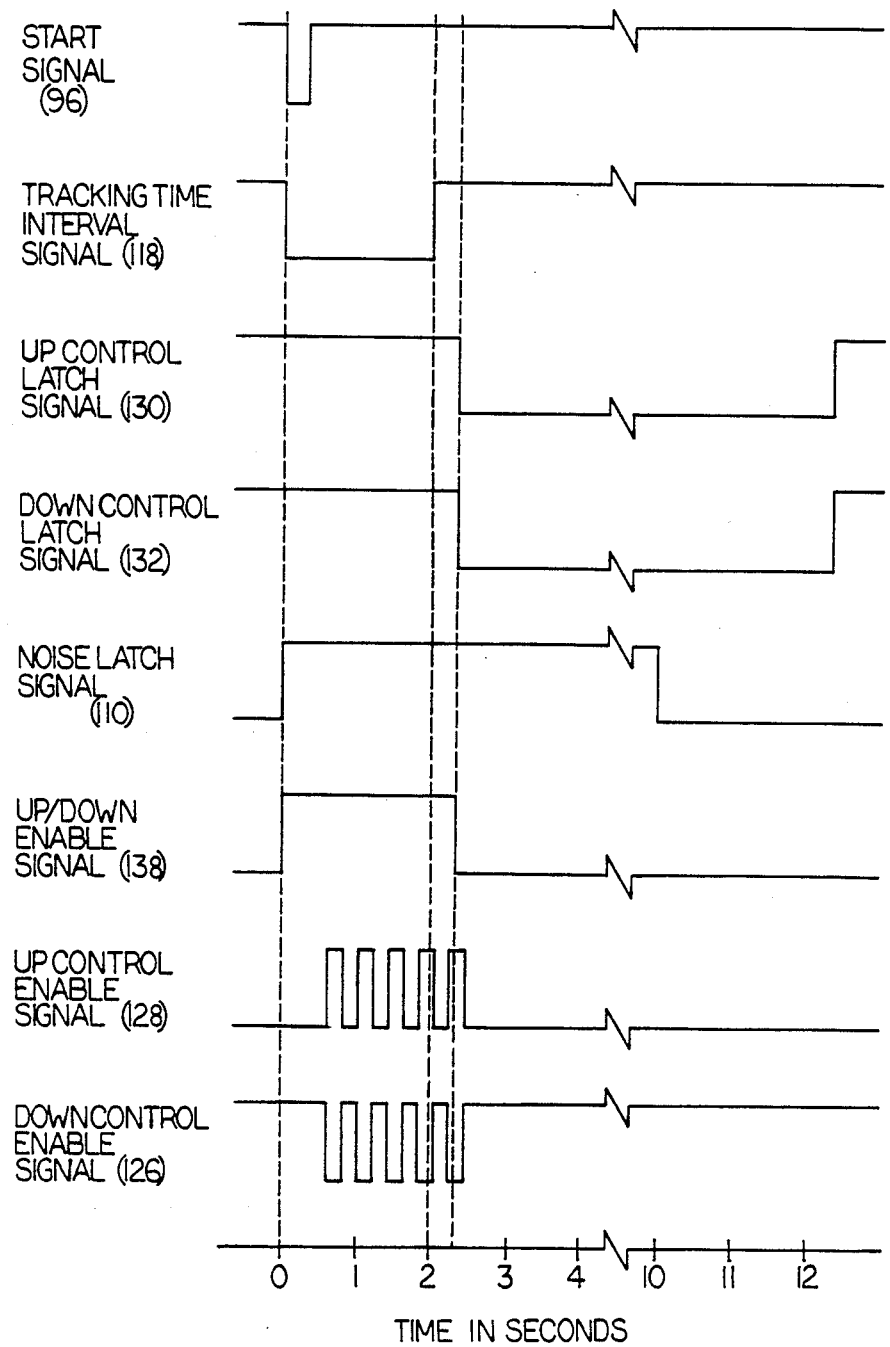

The following operational description of the apparatus 10 is best understood by frequent reference to FIGS. 5 and 6. FIG. 5 shows the signal produced at the analog output terminal 70 with respect to time. The signal depicted is analogous to the representation produced on the chart recorder. FIG. 6 is a signal timing diagram illustrating the logical status of various signals throughout the apparatus 10 with relation to time.

The first and second monostable multivibrators 98,120 of the pulse enable circuit 42 are activated in response to a logic "low" signal from the start switch 44. A logic "low" tracking time interval signal is produced at the second output terminal 118 of the first monostable multivibrator 98, resetting the second monostable multivibrator 120 and producing logic "high" direction control latch signals at the first and second output terminals 130,132 of the second monostable multivibrator 120. These signal conditions remain static for the duration of the tracking time interval signal, established by the adjustment of the tracking time potentiometer 106. In the example of FIG. 6, the tracking time interval is established at 2 seconds. Coincident with receiving the logic "low" signal from the start switch 44, a logic "high" noise latch signal having a duration established by the first R/C time delay circuit 100, is also produced at the first output terminal 110 of the first monostable multivibrator 98. In FIG. 6, this time duration is preferably 10 seconds.

Each of the direction control latch signals and the noise latch signal is delivered to the first input terminal 114 of the fourth operational amplifier 116 through respective resistors 112, 134, 136. Owing to the value selection of the resistors 112, 134, 136, the fourth operational amplifier 116 functions as a logical "AND" gate, and produces a logic "high" up/down enable signal at the gate output terminal 138 only in response to each of the received signals having a corresponding logic "high" status. Conversely, in response to any one of the received signals having a logic "low" status, the up/down enable signal produced at the gate output terminal 138 switches to a logic "low" level. The up/down enable signal is coupled to the pulse control circuit 40.

The comparator 38 of the control means 36 receives both the actual power signal from the signal conditioner 22 and the desired power signal from the settable means 34, and produces a first motor control signal in response to the magnitude of the desired power signal being greater than the magnitude of the actual power signal, and a second motor control signal in response to the magnitude of the desired power signal being less than the magnitude of the actual power signal. Since the sonic power supply 14 provides electric power having a substantially constant voltage to the sonic generator means 16, the amount of sonic power supplied to the workpiece 12 is responsive to the distance between the sonic generator means 16 and the workpiece 12.

Assuming that the actual power signal delivered to the comparator 38 is less than the desired power signal delivered from the settable means 34 at the time the start switch 44 is depressed, the comparator 38 produces the first motor control signal required to operate the motor means 26 to move the sonic generator means 16 closer to the workpiece 12. This is shown in FIG. 6 as a logic "high" down control enable signal produced at the output terminal of the third operational amplifier 76. Conversely, assuming that the actual power signal delivered to the comparator 38 is greater than the desired power signal delivered from the settable means 34 at the time the start switch 44 is depressed, the comparator 38 produces the second motor control signal required to operate the motor means 26 to move the sonic generator means 16 away from the workpiece 12. This is shown in FIG. 6 as a logic "high" up control enable signal produced at the output terminal of the second operational amplifier 74.

In response to receiving the first and second motor control signals from the comparator 38, the up/down enable signal from the pulse enable circuit 42, and the motor speed control signal from the speed generator 46, the pulse control circuit 40 passes the motor control signals to the motor driver 30, and the motor 28 responsively moves the sonic generator means 16 relative to the workpiece 12.

As the sonic generator means 16 approaches the workpiece 12, the degree of acoustic coupling increases and the total power consumed by the sonic generator means 16 likewise increases. In response to the actual power signal and the desired power signal being substantially equal, the control means 36 causes the sonic generator means 16 to begin "tracking" the workpiece 12. In other words, as the workpiece 12 begins to erode owing to the application of sonic power, the sonic generator means 16 maintains a coupling distance from the workpiece 12 sufficient to sustain the desired power consumption. This is shown in FIG. 6 by the toggling of the up and down control enable signals produced at the outputs of the second and third operational amplifiers 74,76. This is also shown in the graphic representation of FIG. 5 as the initial 2 seconds of the represented curves. The duration of the tracking mode is controlled by the duration of the tracking time interval signal, which, as described above, is responsive to the adjustment of the tracking time potentiometer 106.

Upon the termination of the tracking time interval, the tracking time interval signal produced at the second output terminal 118 of the first monostable multivibrator 98 again assumes a logic "high" level. Responsively, upon the next transition of either the up or down control enable signals received at the third and fourth input terminals 126,128 of the second monostable multivibrator 120, the up and down direction control latch signals proceed to logic "low" states for periods determined by respective R/C time delay circuits 122,124, and the up/down enable signal produced at the gate output terminal 138 assumes a logic "low" state. In response to receiving the logic "low" up/down enable signal, the pulse control circuit 40 blocks delivery of motor control signals to the motor means 26 from the comparator 38.

In the event that the desired power magnitude is not achieved during the predetermined tracking time interval, the up and down control enable signals fail to toggle the up and down control latch signals to the logic "low" level. Responsively, the up/down enable signal is maintained at the logic "high" status, and the apparatus 10 continues to automatically move the sonic generator means 16 toward the workpiece 12 until the noise latch enable signal makes the transition to the logic "low" level. The test can then be restarted, with the sonic generator means 16 at a relatively closer position to the workpiece 12.

Assuming that the tracking mode is achieved and the tracking time interval expires, the sonic power delivered from the sonic generator means 16 to the workpiece 12 continues to erode the surface of the workpiece 12, but the motor means 26 is blocked from moving the sonic generator means 16 closer to the workpiece 12. Responsively, the acoustic coupling between the sonic generator means 16 and the workpiece 12 decreases, and the power consumed by the sonic generator means 16 likewise decreases. This is readily seen in FIG. 5 where, following the initial 2 second tracking period, the actual power signal delivered to the chart recorder from the analog output terminal 70 decreases with respect to time. Both the absolute amount of actual power decrease, and the slope of the curve depicting the power decrease, are responsive to the rate of erosion of the workpiece 12 material. Therefore, the rate of actual power consumption decrease is inversely proportional to the rate of erosion of the workpiece 12 material. The two curves shown in FIG. 6 represent respective acceptable and unacceptable material compositions.

Once a range or family of power curves representing acceptable quality workpiece material is identified by empirical means, no subjective analysis of the degree of erosion of the workpiece is required to interpret the material test results. Owing to the controllability of the apparatus 10, even an unskilled operator can reliably produce consistent, objective test results.

Those skilled in the art will recognize that the control means 36 of the instant invention is capable of implementation utilizing a data processor in lieu of the discrete components described above. Such a data processor, programmed with suitable software, can perform the identified tasks of signal comparison and motor control. In addition, if a more fully automated system is desired, a data processor can analyse the data produced, according to predetermined actual power curves, and automatically determine the relative quality of various workpieces being evaluated. Such a data processor based system is believed to fall within the purview of the appended claims. However, it is believed that the above described apparatus fully responds to the identified problems associated with material testing.

Other aspects, objects, advantages and uses of this invention can be obtained from a study of the drawings, the disclosure, and the appended claims.

We claim:

1. Apparatus for controllably delivering power from a device to a workpiece, comprising:
   power means for supplying electrical power;
   sonic generator means for controllably supplying sonic power to said workpiece in response to said power supply means;
   means for sensing the amount of power consumed by said sonic generator means and producing an actual power signal having a magnitude responsive to said sensed power;
   motor means for controllably moving said sonic generator means relative to said workpiece in response to receiving motor control signals;
   settable means for producing a desired power signal having a controlled magnitude; and,
   control means for comparing the magnitudes of said desired power and said actual power signals, delivering motor control signals to said motor means in response to the magnitudes of said compared power signals during a predetermined tracking time period, and blocking the delivery of said motor control signals to said motor means in response to termination of said tracking time period.

2. Apparatus, as set forth in claim 1, wherein said control means produces a first motor control signal in response to the magnitude of said desired power signal being greater than the magnitude of said actual power signal and a second motor control signal in response to the magnitude of said desired power signal being less than the magnitude of said actual power signal.

3. Apparatus, as set forth in claim 1, wherein said power means supplies electric power having a substantially constant voltage, and the amount of sonic power supplied to said workpiece is responsive to the distance between said sonic generator means and said workpiece.

4. Apparatus, as set forth in claim 1, including means for displaying a free air power level of said sonic generator means, the magnitude of said desired power signal being offset by an amount substantially equal to the displayed magnitude of said free air power level.

5. Apparatus, as set forth in claim 4, wherein said display means is adapted to alternatively display the magnitude of at least one of said desired and actual power levels.

6. Apparatus for testing a workpiece, comprising:
   power means for supplying electrical power having a substantially constant voltage;
   sonic generator means for controllably supplying sonic power to said workpiece in response to said power supply means and to being acoustically coupled to said workpiece;

means for sensing the amount of power consumed by said sonic generator means and producing an actual power signal having a magnitude responsive to said sensed power;

motor means for controllably moving said sonic generator means relative to said workpiece in response to receiving motor control signals;

settable means for producing a desired power signal having a controlled magnitude;

means for controllably producing a tracking time interval signal for a predetermined period of time; and, control means for receiving said desired power signal, said actual power signal, and said tracking time interval signal, comparing said desired power and said actual power signals, supplying a first motor control signal in response to the magnitude of said desired power signal being greater than the magnitude of said actual power signal and to receiving said tracking time interval signal, supplying a second motor control signal in response to the magnitude of said desired power signal being less than the magnitude of said actual power signal and to receiving said tracking time interval signal, and blocking said motor control signals in response to failing to receive said tracking time interval signal.

7. A method for testing a workpiece, comprising the steps of:
(A) delivering electric current having a substantially fixed voltage from a power means to a sonic generator means;
(B) producing a sonic vibration having a predetermined frequency and amplitude, in response to receiving said electric current;
(C) sensing the amount of power consumed by said sonic generator means;
(D) moving said sonic generator means relative to said workpiece in response to said sensed power failing to substantially equal a predetermined desired power level, and to a predetermined period of time;
(E) blocking movement of said sonic generator means relative to said workpiece in response to termination of said predetermined period of time; and,
(F) substantially continuously displaying the amount of power consumed by said sonic generator means with respect to said predetermined period of time.

* * * * *